United States Patent [19]

Zdrodowski

[11] 4,162,689

[45] Jul. 31, 1979

[54] TIME DIVISION FLOW CONTROL

[75] Inventor: Joseph J. Zdrodowski, Nutley, N.J.

[73] Assignee: Hoffmann-La Roche Inc., Nutley, N.J.

[21] Appl. No.: 815,469

[22] Filed: Jul. 14, 1977

[51] Int. Cl.² .............................................. G01F 11/00
[52] U.S. Cl. ..................................... 137/266; 137/88; 137/624.12; 137/624.11; 422/100
[58] Field of Search ................. 23/230 R, 253 R, 259, 23/292; 137/88, 624.12, 624.11, 266; 422/100

[56] References Cited

U.S. PATENT DOCUMENTS

| 3,230,048 | 1/1966 | Skeggs .............................. 23/230 X |
| 3,488,154 | 1/1970 | Hronas .............................. 23/230 R |
| 3,557,077 | 1/1971 | Brunfeldt et al. ................. 23/259 X |
| 3,846,075 | 11/1974 | Cioffi ................................ 23/259 X |

*Primary Examiner*—R. E. Serwin
*Attorney, Agent, or Firm*—Jon S. Saxe; George M. Gould

[57] ABSTRACT

Calibrated control of the duty cycle of fast acting pulse valves provides highly accurate control of fluid flow through the valve. While the flow is precisely controllable, it is not directly proportional to the duty cycle and thus a calibration curve is needed for each valve.

10 Claims, 6 Drawing Figures

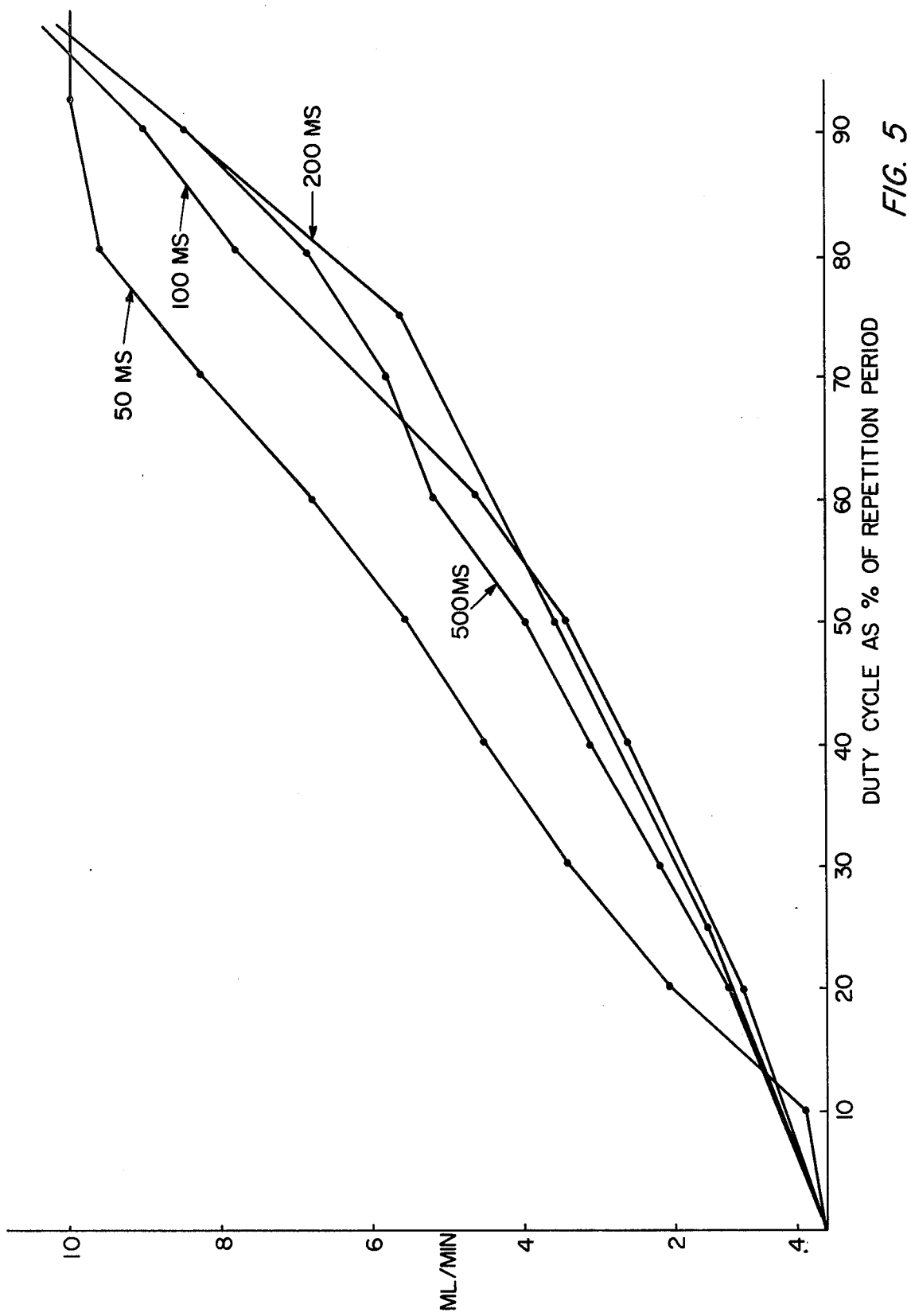

TIME DIVISION FLOW CONTROL

BACKGROUND OF THE INVENTION

A time division blending system is described in U.S. Pat. No. 4,004,884. In such system, different fluids from a plurality of reservoirs are blended sequentially opening and closing valves in the outlet lines leading from each reservoir for a fixed time ratio of the total valve cycle period. The amount of each different fluid obtained in the final fluid stream is directly proportional to the time the corresponding valve is open during said cycle. One is thus able to obtain reproducible and highly accurate concentrations of a number of different fluids in the final fluid system.

DESCRIPTION OF THE INVENTION

The present invention relates to a novel method for accurately controlling fluid flow rates utilizing time division control of pulse valves. This invention is particularly useful in controlling relatively low fluid flow rates such as 60 ml/hr or less.

Accurate control of fluid flow rates is important in numerous devices. Thus, for example, such control is extremely desirable in liquid chromatography with respect to buffer flow, in analytical monitoring devices such as fluorescence monitors with respect to buffer and reagent flow and in infusion devices providing medication by intravenous drip. In presently existing devices fluid control is usually performed by use and adjustment of a needle valve or in the case of devices having fluid reservoirs, by pressuring the reservoirs and controlling fluid flow by adjusting the pressure of the system. These methods of fluid control suffer from the deficiencies of insufficient accuracy, non-reproducibility due to drift or fluctuations and difficulty of automating the control of fluid flow.

The present invention provides a convenient method and system for controlling low flow rate fluid flow which is accurate, reproducible and which can be readily automated. Control is achieved electronically using the principle of time divided flow. In embodiments wherein a plurality of fluid streams are being blended into a single outlet stream, time division fluid flow is achieved by shortening the duty cycle of each valve controlling the flow of each of said fluid streams but maintaining the same repetition period.

Alternatively, the fluid flow of a single fluid stream can be independently controlled through time division by utilizing a fast acting pulse valve (2–5 millisecond response time) pulsed at a rapid rate, i.e., 1 pulse per second or greater. Under such conditions the duty cycle of the valve would control the fluid flow since time becomes the variable in the equation $$F = V \times T$$

where F is fluid flow rate, V is volume and T is time.

It should be noted that when operating at a repetition period of between ½ and 1 second some means of dampening the pulse of the outlet fluid stream should be introduced into the system. This can be accomplished by using commercially available pulse dampeners, by introducing flexible tubing into the outlet line from the pulse valve or by any other means known in the art to effectuate pulse dampening.

Although theoretically one would expect that the flow rates obtained by the utilization of time divided control in either of the aforesaid embodiments would be calculable, experimental evidence of the measurement of full flow versus time divided flow indicate that the overall flow is not directly proportional to the duty cycle of the valves. However, the flow was in fact precisely controllable within the indicated range of operability.

BRIEF DESCRIPTION OF THE DRAWINGS

The present invention is further illustrated by reference to the accompanying drawings. FIG. 5 is a graphic representation of fluid flow observed by operating a pulse valve at various duty cycles with a single fluid stream time division flow control system.

Figure 1:
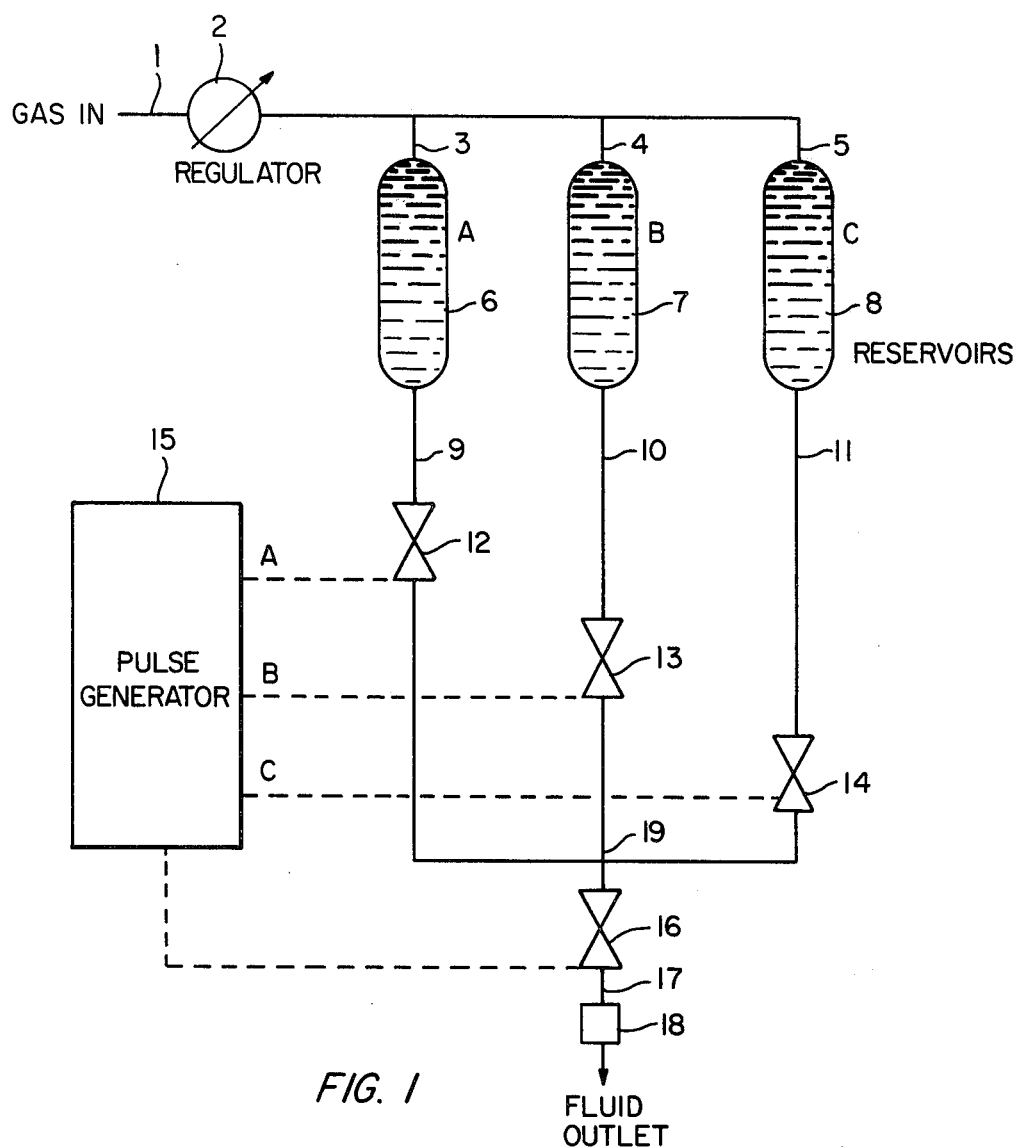
FIG. 1 is a schematic representation of a time division flow control system in a blending embodiment. A graphic view of the pulse signal control used in a time division blending system such as described in U.S. Pat. No. 4,004,884 is shown in FIG. 2.

Turning first to FIG. 1, fluids are stored in reservoirs 6, 7 and 8, optionally under pressure via gas inlet 1 regulated by gas regulator 2. The present system can also operate under gravity flow conditions and thus elements 1 and 2 can be eliminated from the system under such circumstances. Unlike prior art systems, the use of pressure conditions is not intended to control fluid flow but to provide optimum flow conditions within the system. Fluid from each of the indicated reservoirs flows out through lines 9, 10 and 11 and through pulse valves 12, 13 and 14 respectively. The duty cycle of each such valve is controlled electronically by signals provided by pulse generator 15. Suitable pulse generators useful in the practice of the invention are articles of commerce.

The pulse valves utilized in the present invention can be conventional miniature three way valves having response times of 2 to 5 milliseconds and having long life characteristics. A particularly preferred valve for this purpose is commercially available from the Lee Company and designated an LIF valve. Such valve has a response time of 3 milliseconds and a rated life of 200 million cycles.

Accurate and reproducible concentrations of each of the fluid streams are then obtained in a resulting fluid stream by joining the individual streams via a tee connection 19. Control of the concentrations of the respective fluids in the final fluid stream is achieved by controlling the duty cycles of each of the valves 12, 13 and 14 to a fixed ratio of each other. Thus, if it is desired that the final stream contain, for example, 20% fluid A, 30% fluid B and 50% fluid C then valve 12 would have a duty cycle of 20% of the total duty cycles of the three valves, while valve 13 would have a 30% duty cycle and valve 14 would have a 50% duty cycle each on the same basis.

The final fluid stream is then passed out through outlet line 17 which is provided with an optional dampening means 18. As indicated previously such dampening means can be a commercial pulse dampener, flexible tubing or other equivalent means known in the art to effect fluid pulse dampening. Such dampening means would be utilized when the pulse rates of the three control valves are in the range of 1 to 2 pulses per second.

Figure 2:
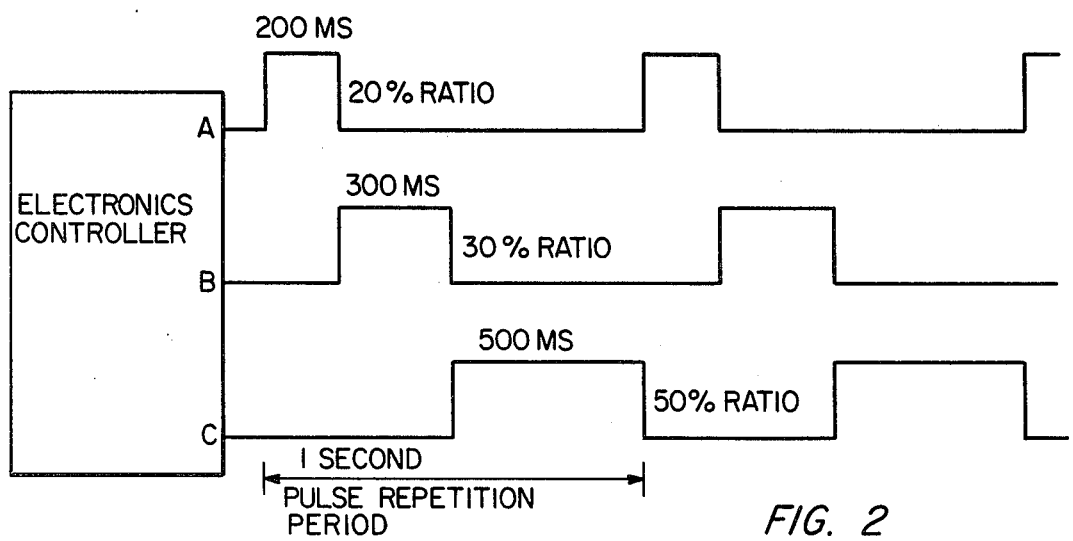

In addition, the system may also contain an optional pulse valve 16 located downstream of tee 19. In such an embodiment, valves 12, 13 and 14 are utilized in a time division blending configuration. A representative graphic view of the valve control pulses in such an embodiment is shown in FIG. 2 and is essentially the method and system described in U.S. Pat. No. 4,004,884. The final fluid stream passing out of tee 19 will thus have a configuration of 20% fluid A, 30% fluid B and 50% fluid C. Control of the flow rate of the final fluid stream is accomplished by operating valve 16 in a time division fluid control manner, that is by pulsing valve 16 at a rate of 1 pulse per second or greater. This mode of operation will be further discussed with respect to FIG. 4.

While the system shown in FIG. 1 contains three fluid streams it should be understood that the number of fluid streams which can be controlled by the system and method of this invention is not narrowly critical and can conveniently range from 1 to about 20 channels. However, this limit only relates to the hardware limitations and multiple groups could be incorporated thereby allowing any number of channels.

FIG. 2, as discussed briefly previously, presents a graphic view of the pulse pattern derived from an electronics controller and used to control valves in a time division blending configuration as set forth in one embodiment of FIG. 1. Maintenance of a fixed ratio between the duty cycles of the three valves under control provides a final fluid stream containing each of the component fluids in exact proportion; 20% fluid A, 30% fluid B and 50% fluid C. To be noted is the fact that in such configuration the total duty cycles of the three valves equals the pulse repetition period, i.e., 200 milliseconds + 300 milliseconds + 500 milliseconds = 1 second.

Figure 3:
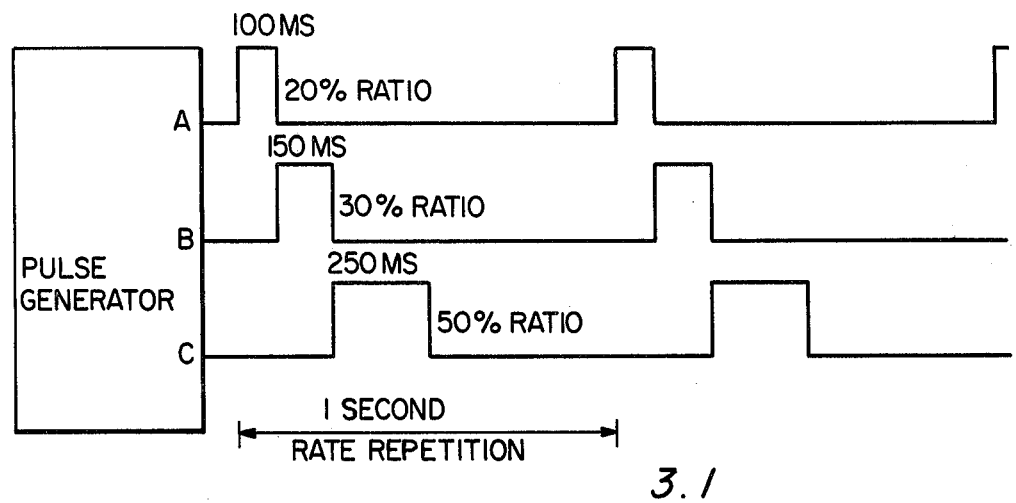
In FIG. 3 graphic views of alternate pulse signal controls used in the blending embodiment is depicted.
Figure 3:
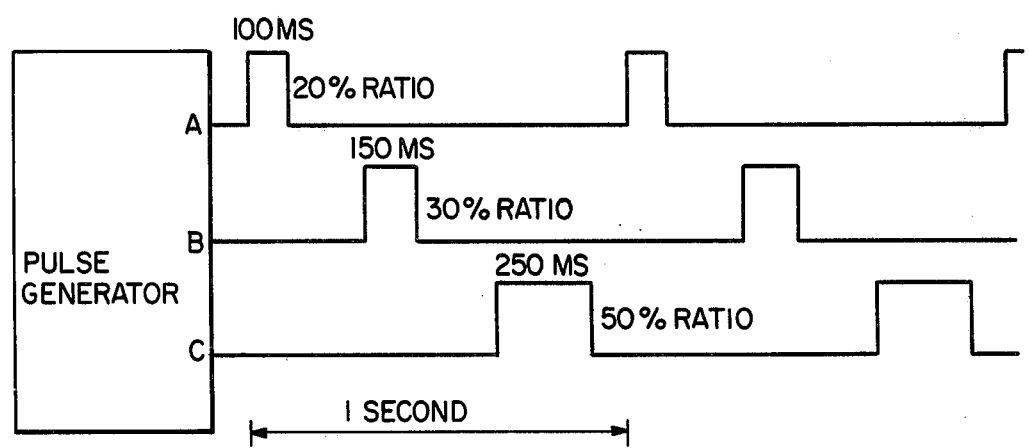

In FIG. 3 the pulse pattern produced by a pulse generator in two operating embodiments of the time division flow control system used with a plurality of fluid streams is shown. Turning first to embodiment 3.1, it is seen that in comparison with the pulse pattern in FIG. 2, the duty cycle of each valve has been reduced by a factor of $\frac{1}{2}$ but the duty cycle ratios have been maintained so that the final fluid stream will contain the same concentrations of the three fluids as in the FIG. 2 mode. Furthermore, the total duty cycles of the three valves is 500 milliseconds which is only half of the 1 second repetition period. Thus in the remaining one half second all three valves are in an off position to flow.

An alternative pulse pattern useful in achieving time division flow control in a multi-fluid stream is graphically shown in FIG. 3.2. Again as in FIG. 3.1 the duty cycles for the three valves are 100 milliseconds, 150 milliseconds and 250 milliseconds respectively. However, instead of the three pulses being propagated in consecutive fashion with a single "off" period to complete the repetition period of one second, the pulse generator is adapted to introduce an off period between each pulse. The length of each of these intermittent off periods is not critical; provided, of course, that the total of such off periods and the sum of the duty cycles of the valves used in the system equals the repetition period.

One advantage for the FIG. 3.2 embodiment over other pulse modes is the fact that the divided off period results in less ripples in the final fluid stream. Such advantage is particularly important when the fluid flow is ultimately used in analytical instruments since the presence of ripples in such fluid stream will result in undesired perturbations in the instrument's baseline.

Figure 4:
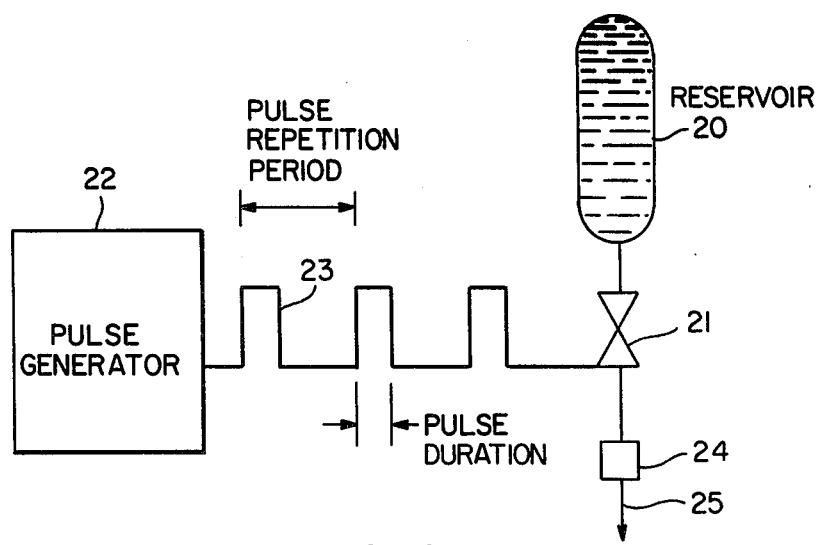
FIG. 4 is a schematic representation of a time division flow control system used in a single fluid stream embodiment.

FIG. 4 represents a schematic view of a time division flow control system in a single fluid stream embodiment. Fluid flow from reservoir 20 is controlled by pulse valve 21. Control pulse 23, shown graphically, are generated by pulse generator 22 and control the duty cycles of valve 21. As seen in FIG. 4, the duty cycle is maintained at only a proportion of the repetition period and thus for a substantial portion of the period valve 21 is in the off position. Flow control is achieved by utilizing a pulse repetition rate greater than 1 per second. If the repetition rate is between 1 and 2 per second then a pulse dampener 24 is introduced into fluid stream outlet line 25.

Calibration curves for various duty cycles of a pulse valve set into a single fluid stream system are graphically shown in FIG. 5. The pulse valve used was a Lee Company LIF valve and duty cycles of 50 milliseconds, 100 milliseconds, 200 milliseconds and 500 milliseconds. Fluid used in the test was water and the conditions employed were a pressure of 20 in. of water and a temperature of 22° C. Parameters plotted were fluid flow in 0-10 milliliters per minute against the duty cycle percent of repetition period employed. The fluid flow observed is proportional to the duty cycle but not in a direct linear manner. However, the values observed for a given valve under the same external conditions are consistently reproducible and thus the system can be calibrated in an exact manner. Thus any desired flow rate can thereafter be achieved by merely adjusting the pulse generator to provide the requisite duty cycle and repetition period.

It is within the skill of the art to introduce data such as set forth in FIG. 5 into a suitable computer and program such computer to select and control the appropriate repetition period and duty cycle for each valve in the system to thereby produce the desired flow conditions. A closed loop system can also be employed wherein downstream parameters are monitored and the requisite flow conditions changed to meet the differing requirements of the instrument or device.

I claim:
1. A time division fluid flow system comprising in combination:
   (A) one or more fluid stream inlet means, each fluid stream inlet means providing a fluid stream,
   (B) pulse generator means;
   (C) one or more pulse valve means, wherein one said pulse valve means is in operative relationship to one of said fluid stream inlet means, said pulse valve means being under control of said pulse generator means as to their respective duty cycles whereby a final fluid stream derived from the aforesaid fluid stream is provided under time division flow control when the repetition period of said pulse valve means is less than one second and the sum of the duty cycles of said pulse valves is less than the repetition period.
2. The system of claim 1 wherein the final fluid stream flow rate is less than 60 ml per hour.
3. The system of claim 1 wherein the repetition period is between $\frac{1}{2}$ and 1 second and a pulse dampening means is introduced downstream of said pulse valve means.
4. The system of claim 1 wherein a single fluid stream inlet means is present.

5. The system of claim 1 wherein a plurality of fluid stream inlet means and a corresponding number of pulse valve means are present, said fluid streams being merged into a single final fluid stream.

6. The system of claim 5 wherein the duty cycles of the plurality of pulse valve means are controlled to be contiguous with a single off period during each repetition period.

7. The system of claim 5 wherein the duty cycle of the pulse valve means are controlled to be non-contiguous with an off period between each.

8. The system of claim 5 wherein the final fluid stream is a blend of the fluid streams provided by said fluid stream inlet means, the concentration of each said fluid streams in said final fluid stream being directly proportional to the percent of the duty cycle of the pulse valve means controlling said fluid stream of the total duty cycles of all the pulse valve means in the system.

9. In a time division blending system having in combination:
(A) a plurality of fluid stream inlet means each carrying a different fluid stream;
(B) electronic controller means;
(C) a plurality of valve means corresponding in number to said fluid stream inlet means, one said valve means being in flow control relationship to each said fluid streams, said valve means being controlled electronically by said electronic controller means so as to provide duty cycles for each valve means which are in a proportionate ratio to the desired concentrations of each fluid stream in a final fluid stream;
(D) tee means for blending the fluid streams derived from each of said valve means; and
(E) final fluid stream outlet means wherein a final fluid stream is provided containing a desired concentration of each component fluid stream;

the improvement comprising providing said system with a pulse valve means located in said final fluid stream outlet means and a pulse generator means, said pulse valve means being under control of said pulse generator means as to its duty cycle whereby said final fluid stream is under time division flow control when the repetition period of said pulse valve means is less than one second and the duty cycle is less than said repetition period.

10. The improved system of claim 9 wherein said repetition period is between ½ and 1 second and a pulse dampening means is introduced downstream of said pulse valve means.

* * * * *